United States Patent [19]

Ascione

[11] Patent Number: 5,670,137
[45] Date of Patent: Sep. 23, 1997

[54] ANHYDROUS DENTIFRICE COMPOSITION

[75] Inventor: Jean Marc Ascione, Paris, France

[73] Assignee: L'Oreal, Paris, France

[21] Appl. No.: 354,908

[22] Filed: Dec. 12, 1994

[51] Int. Cl.$^6$ .............................. A61K 7/16; A61K 7/18; C08B 11/08
[52] U.S. Cl. .................... 424/49; 424/50; 424/52; 424/53; 536/90
[58] Field of Search .......................... 424/49–58

[56] References Cited

U.S. PATENT DOCUMENTS

| | | | |
|---|---|---|---|
| 3,691,272 | 9/1972 | Asche | 424/57 |
| 4,071,615 | 1/1978 | Barth | 424/52 |
| 4,096,241 | 6/1978 | Geistlich et al. | 424/54 |
| 4,228,277 | 10/1980 | Landoll | 536/90 |
| 4,485,089 | 11/1984 | Leipold | 424/49 |
| 4,565,692 | 1/1986 | Mulvey et al. | 424/57 |
| 4,584,189 | 4/1986 | Leipold | 424/54 |
| 5,000,989 | 3/1991 | Ford | 427/387 |
| 5,093,138 | 3/1992 | Drew et al. | 426/88 |
| 5,120,528 | 6/1992 | Chang et al. | 424/49 |
| 5,176,901 | 1/1993 | Gallop et al. | 424/54 |
| 5,192,529 | 3/1993 | Garlick et al. | 424/49 |

FOREIGN PATENT DOCUMENTS

| | | |
|---|---|---|
| 0138615 | 4/1985 | European Pat. Off. . |
| 0384167 | 8/1990 | European Pat. Off. . |
| 0412705 | 2/1991 | European Pat. Off. . |

*Primary Examiner*—Shep K. Rose
*Attorney, Agent, or Firm*—Jacobson, Price, Holman & Stern, PLLC

[57] ABSTRACT

The invention concerns a dentifrice composition containing, in an anhydrous medium which comprises glycerin, at least one hydroxyethylcellulose having at least one hydrophobic chain, and at least one pyrogenetic silica with an average primary particle size of less than 40 nm; as well as its use in bucco-dental hygiene.

10 Claims, No Drawings

ANHYDROUS DENTIFRICE COMPOSITION

The present invention relates to new anhydrous dentifrice compositions based on glycerin, hydroxyethylcellulose with a hydrophobic chain, and pyrogenetic silica, and to their use in bucco-dental hygiene.

Dentifrices are well known in the prior an, and must combine several properties, concerning appearance, such as homogeneity, rheology, preservation, foaming capacities, and cleaning and polishing properties.

Attempts are made in particular to obtain compositions which, in use, display a smooth, homogeneous bright appearance, have a constant viscosity, a consistency suitable to form a ribbon, adhering to the toothbrush but not spreading too much. These compositions must also display high cleaning and polishing capacity, to confer a shine on the enamel, while exhibiting low abrasiveness to the dentin.

The dentifrice compositions of the prior an are usually in aqueous form, and this can raise problems connected with the use, in such dentifrices, of active agents that are slightly stable or unstable in aqueous medium, such as enzymes, bleaching agents, oxygen liberators, vitamins etc. The compositions often require the use of preservatives.

U.S. Pat. No. 4,071,615 describes anhydrous dentifrice compositions based on glycerin, thickeners such as hydroxyethylcellulose and carboxymethylcellulose, and silica.

These compositions present the drawback of insufficient consistency, and the compositions prepared with the use of the thickeners mentioned exhibit a runny character that is difficult to accept for a dentifrice.

Patent No. EP.A. 138,615 describes the use of thickening silica having a grain size distribution of 2 to 20 µm.

The composition described in this document, which make use of precipitated or pyrogenetic silicas with a grain size distribution of 2 to 20 µm, have the drawback of giving rise, in anhydrous medium, to compositions with insufficient viscosity and poor shelflife.

The Applicant has developed a new anhydrous dentifrice composition which permits the introduction of active agents that are slightly stable or unstable in aqueons medium, and which, in use, exhibits the aforementioned smooth, homogeneous, bright characteristics, viscosity, consistency and cleaning and polishing capacity. The composition also has the advantage of good shelflife. According to the invention, and throughout the following description, anhydrous composition means a composition containing less than 3% by weight of water. This very low proportion of water is due to the traces of water present in certain raw materials used according to the invention.

The Applicant, has discovered in particular that the incorporation, in an anhydrous dentifrice composition containing glycerin, of at least one hydroxyethylcellulose with a hydrophobic chain and at least one pyrogenetic silica with an average primary particle size less than 40 nm, made it possible to prepare a dentifrice composition exhibiting the aforementioned qualifies and characteristics, and helping to solve the problems raised by the dentifrices of the prior art. The anhydrous dentifrice compositions of the invention offer the advantage of permitting the introduction of active agents that are slightly stable or unstable in aqueous medium, and do not require the use of a preservative. These compositions also haw the requisite properties for a dentifrice, particularly rheological, that is to say a sufficient consistency in handling and permitting the spreading of the dentifrice on the toothbrush, and a brittleness permitting the curling of the ribbon of dentifrice at the end of spreading. They also display good foaming, cleaning, polishing and abrasion properties.

These compositions also exhibit good homogeneity and are particularly bright and easily dispersible in the mouth.

The invention therefore bas for object an anhydrous dentifrice composition based on glycerin, hydroxyethylcellulose with a hydrophobic chain, and pyrogenetic silica with an average primary particle size of less than 40 nm.

The invention also has for object the use of such a composition in bucco-dental hygiene.

Another object of the invention consists of a tooth cleaning process making use of such a composition.

Other objects and advantages of the invention will be apparent from the following description and examples.

The dentifrice composition of the invention is essentially characterized by the fact that it contains, in an anhydrous medium comprising glycerin, at least one hydroxyethylcellulose containing at least one hydrophobic chain, and at least one pyrogenetic silica with an avenge primary particle size of less than 40 nm.

The hydroxyethylcellulose with hydrophobic chains which are particularly suitable for the invention are hydroxyethylcellulose which have been modified by the introduction of a hydrophobic alkyl or aralkyl group. Hydroxyethylcellulose generally have a molecular weight of between 1000 and 1,000,000, and preferably between about 50,000 and 500,000. They have an average degree of substitution of hydroxyethyl groups between 2 and 4 per cellulose anhydroglucose unit of the cellulose molecule.

The hydrophobic alkyl or aralkyl chain can be attached to the cellulose ether substrate by means of an ether, ester or urethane bond, and ether bonds are preferable.

The substitution rate of hydrophobic groups varies between about 0.2% by weight with respect to the weight of the cellulose other and the value that causes a water solubility of the cellulose ether of loss than 1% by weight.

The alkyl group preferably has 10 to 24 carbon atoms. The aralkyl groups preferably designate an alkyl ($C_6$–$C_{20}$) phenyl group such as nonylphenol, dodecylphenyl.

Products of this type and their preparation are described more fully in U.S. Pat. No. 4,228,27, EP.A.0.412.705 and EP.A.01.38.615.

Such hydroxyethylcellulose with hydrophobic chains are marketed in particular under the names of Natrosol Plus Grade 330-CS and Polysurf 67 by the Aqualon company.

The product Natrosol Plus Grade 330-CS is a hydroxyethylcellulose substituted by 0.4 to 0.8% by weight of cetyl groups. The degree of molar substitution by hydroxyethyl is between 3 and 3.7, and the molecular weight before chemical modification is about 300,000.

Polysurf 67 is substituted by 0.4 to 0.6% of cetyl groups with respect to the weight of the hydroxyethylcellulose, and the degree of molar substitution by hydroxyethyl groups is between 2.2 and 2.8.

According to the invention, it is also possible to use hydroxyethylcellulose containing an aralkyl hydrophobic chain, such as described in particular in Patent No. EP.A.0384.167. One example is the product marketed under the name Amercell Polymer HM-1500 by the Amerchol company, and which is a hydroxyethylcellulose modified by a nonoxynyl (nonylphenol) group.

It is preferred to use hydroxyethylcellulose with hydrophobic chains in concentrations between about 0.01 and 2% by weight, and preferably between 0.05 and 0.5% by weight with respect to the total weight of the composition.

The pyrogenetic silicas that can be used for the invention have an avenge primary particle size of less than 40 nm, and preferably not more than 30 nm, and they may be hydrophilic or hydrophobic. The average primary particle size is preferably between 5 and 30 nm.

Among the hydrophilic pyrogenetic silicas which have an average primary particle size less than 40 nm are the products marketed under the names Aerosil 90, Aerosil 130, Aerosil 150, Aerosil 200, Aerosil 300 and Aerosil 380 by the Degussa company, and the product marketed under the name CAB-O-SIL-M-5 by the company Cabot.

Among the hydrophobic pyrogenetic silicas with an avenge primary particle size less than 40 nm are the products marketed under the names Aerosil R202, Aerosil R805, Aerosil R812, Aerosil R972 and Aerosil R974 by the company Degussa, and the product marketed under the name CAB-O-SIL-TS 720 by the Cabot company.

According to the invention it is preferable to use pyrogenetic silicas of the hydrophobic type.

Pyrogenetic silicas are present in the compositions of the invention in a concentration of between 2 and 10% by weight, and preferably between 4 and 8% by weight with respect to the total weight of the composition.

The glycerin usable for the invention is a pure glycerin, and preferably Codex 99.8% pure glycerin.

Glycerin accounts for more than 50% by weight with respect to the total weight of the composition, and preferably 65 to 90% by weight.

The dentifrice compositions of the invention generally contain a polishing agent in proportions ranging between 2 and 50% by weight, and preferably 4 to 30% by weight with respect to the total weight of the composition. These polishing agents are selected in particular from among inorganic abrasives consisting of one or more compounds, generally insoluble in water and glycerin. Examples include sodium and potassium metaphosphates, calcium phosphate dihydrate, dicalcium phosphate, tricalcium phosphate, calcium pyrophosphate, alma, hydrated aluminas and particularly trihydrated aluminas, silicas different from the pyrogenetic silicas used according to the invention, aluminum and zirconium silicates, bentonite, as well as magnesium orthophosphate and trimagnesium phosphate.

The compositions according to the invention can also contain one or more sufficiently stable and foaming surfactants. These surfactants may be anionic, amphoteric, zwitterionic, cationic or nonionic, and it is preferable to use anionic and/or nonionic surfactants.

In general, the surfactants are present in proportions ranging between 0.1 and 5%, and preferably between 0.5 and 3% by weight with respect to the total weight of the composition.

The compositions according to the invention can also contain active agents for mouth hygiene and particularly agents known to destroy bad breath, such as, for example, cyclodextrins or compounds of zinc, which are inorganic or organic salts, such as, for example, zinc halides, zinc acetate, zinc citrate or zinc fluoride, or ketone derivatives such as described in French Patent No. FR.A.2.678.828.

The compositions according to the invention can also contain other additives that are common in the field of mouth hygiene compositions, such as antibiotics, sweeteners, moisteners and refreshants, preservatives, dyes, flavors, aromatizing and sapidity substances and agents, peptizing agents, plasticizers, anti-bacterial or bactericidal agents, vitamins, anti-caries agents, anti-tartar agents, anti-staining agents, anti-plaque agents, cicatrizants, vasomotors, anti-bleeding agents, and gum-active agents.

The anhydrous dentifrice compositions of the invention enable in particular the use of active agents that are unstable or slightly stable in aqueous medium, such as enzymes, oxygen liberators, bleaching agents such as peroxides, bicarbonates and perborates, for example, anti-caries agents like tin fuoride, vitamins and particularly vitamin C which is an essential agent in the synthesis of collagen in the gums.

The sweeteners that can be used include saccharose, lactose, fructose, xylitol, sodium cyclamate, maltose, sodium saccharinate, mixtures of a-glucosyl/steviolglucoside, D-mannitol, Aspartame, Acesulfam K and mixtures thereof. These sweeteners can be present in concentrations of up to 2% by weight with respect to the total weight of the composition.

The moistening agents can include anhydrous sorbitol, di- and tri-glycerin, xylitol, and polyols such as polyethylene glycol, polypropylene glycol and propylene glycol, for example. These moistening agents can be present in proportions of between 0.1 and 5% by weight.

The refreshants include menthol and ethylmaltol.

Although preservatives are not absolutely indispensable in the compositions according to the invention, they can nevertheless be used to guarantee good bacteriological purity of the compositions. They are selected in particular from among methyl parahydroxybenzoate, propyl parahydroxybenzoate, sodium benzoate and other common preservatives. The concentrations am generally less than 0.5% by weight with respect to the total weight of the composition. The aromatizing agents that can be used include essences of mint, anise, eucalyptus, cinnamon, clove, sage, liquorice, or fruits such as lemon, orange, tangerine or strawberry.

Methyl salicylate can also be used for this purpose. The aromatizing substances, if used, can be incorporated in proportions up to 5% by weight with respect to the total weight of the composition.

The antibacterial agents arc agents normally used in this type of composition for oral use. The choice is preferably made of active agents some of which are essential oils, or substances such as chlorhexidine or its salts, such as the digluconate, dichlorohydrate or diacetate of chlorhexidine, alexidine, octenidine and their salts, hexetidine, phenoxyethanol, phenethyl alcohol and triclosan. The antibacterial agents are generally present in proportions of up to 10% by weight with respect to the total weight of the composition, and preferably in proportions between 0.05 and 2% by weight.

In the compositions of the invention, it is also possible to incoporale anti-caries agents, such as sodium monofluorophosphate, sodium and tin fluorides, amine fluorides, and cationic polymer fluorides like those described in particular in French Patent No. FR.A.2.647.012.

The following examples are intended to illustrate the invention, but do not present a limitative character.

EXAMPLE 1

A paste dentifrice with the following composition is prepared:

| | |
|---|---|
| ■ hydrophobic pyrogenetic silica with an average primary particle size of 16 nm sold under the name Aerosil R972 by Degussa | 6.0 g |
| ■ hydroxyethylcellulose modified by a cetyl chain sold under the name Natrosol Plus Grade 330-CS by Aqualon | 0.1 g |
| ■ hydrated silica sold under the name Tixosil 73 by Rhône-Poulenc | 10.0 g |
| ■ sodium laurylsulfate | 1.5 g |
| ■ methyl parahydroxybenzoate | 0.2 g |

| | |
|---|---|
| ■ sodium saccharinate | 0.1 g |
| ■ titanium dioxide | 1.0 g |
| ■ flavors | 0.8 g |
| ■ Codex pure glycerin | sufficient quantity for 100.0 g |

EXAMPLE 2

A paste dentifrice with the following composition is prepared.

This composition is identical to one described in EXAMPLE 1, except that it contains 6 g of hydrophilic pyrogenetic silica with an average primary particle size of 12 nm sold under the name Aerosil 200 by Degussa instead of the pyrogenetic silica Aerosil R972.

EXAMPLE 3

A paste dentifrice with the following composition is prepared.

It is identical to that of EXAMPLE 1, except that it contains 0.1 g of hydroxyethylcellulose modified by a non-oxynyl group sold under the name Amercell Polymer HM-1500 by Amerchol.

EXAMPLE 4

The following composition is prepared:

| | |
|---|---|
| ■ hydrophobic pyrogenetic silica with an average primary particle size of 16 nm sold under the name Aerosil R972 by Degussa | 4.0 g |
| ■ hydroxyethylcellulose modified by a cetyl chain sold under the name Natrosol Plus Grade 330-CS by Aqualon | 0.2 g |
| ■ hydrated silica sold under the name Tixosil 73 by Rhône-Poulenc | 8.0 g |
| ■ sodium laurylsulfate | 1.4 g |
| ■ titanium dioxide | 0.8 g |
| ■ sodium saccharinate | 0.08 g |
| ■ flavors | 0.6 g |
| ■ Codex pure glycerin | sufficient quantity for 100.0 g |

EXAMPLE 5

The following composition is prepared:

| | |
|---|---|
| ■ hydrophobic pyrogenetic silica with an average primary particle size of 16 nm sold under the name Aerosil R972 by Degussa | 2.0 g |
| ■ hydroxyethylcellulose modified by a cetyl chain sold under the name Natrosol Plus Grade 330-CS by Aqualon | 0.5 g |
| ■ hydrated silica sold under the name Tixosil 73 by Rhône-Poulenc | 12.0 g |
| ■ sodium laurylsulfate | 1.0 g |
| ■ titanium dioxide | 0.6 g |
| ■ methyl parahydroxybenzoate | 0.2 g |
| ■ sodium saccharinate | 0.1 g |
| ■ flavors | 0.8 g |
| ■ Codex pure glycerin | sufficient quantity for 100.0 g |

EXAMPLE 6

The following composition is prepared:

| | |
|---|---|
| ■ hydrophobic pyrogenetic silica with an average primary particle size of 16 nm sold under the name Aerosil R972 by Degussa | 8.0 g |
| ■ hydroxyethylcellulose modified by a cetyl chain sold under the name Natrosol Plus Grade 330-CS by Aqualon | 0.05 g |
| ■ hydrated silica sold under the name Tixosil 73 by Rhône-Poulenc | 4.0 g |
| ■ sodium laurylsulfate | 1.8 g |
| ■ titanium dioxide | 1.0 g |
| ■ methyl parahydroxybenzoate | 0.1 g |
| ■ sodium saccharinate | 0.08 g |
| ■ flavors | 0.8 g |
| ■ Codex pure glycerin | sufficient quantity for 100.0 g |

EXAMPLE 7

A paste dentifrice having the same composition as that of EXAMPLE 1 is prepared, using as hydrophilic pyrogenetic silica Aerosil 90 (average primary particle size 20 nm) from Degussa: 6 g.

I claim:

1. An anhydrous dentifrice composition comprising, based on the total weight of the composition:
   at least 50% of glycerin;
   0.01 to 2% of at least one hydroxy ethyl cellulose modified by the introduction of hydrophobic groups selected from the group consisting of $C_{10}$–$C_{24}$ alkyl groups and alkyl ($C_6$–$C_{20}$) phenyl groups, the substitution rate by the hydrophobic groups varying from about 0.2% by weight with respect to the weight of cellulose ether and a value that causes a water solubility of cellulose that it less than 1% by weight;
   2 to 10% of at least one pyrogenic silica having an average primary particle size of less than 40 nm; and
   2 to 50% of a polishing agent.

2. The composition of claim 1 wherein said polishing agent is hydrated silica.

3. The dentifrice composition of claim 1, characterized by the fact that the hydroxyethylcellulose have a molecular weight of between 1000 and 1,000,000, and have an average degree of substitution by hydroxyethyl groups of between 2 and 4 per cellulose anhydroglucose unit of the cellulose molecule.

4. The composition of claim 1, characterized by the fact that they incorporate hydrophilic or hydrophobic pyrogenetic silicas with an average primary particle size of between 5 and 30 nm.

5. The composition of claim 1, characterized by the fact that it further contains one or more foaming surfactants.

6. The composition of claim 1, characterized by the fact that it also contains active agents for oral hygiene.

7. The composition of claim 1, characterized by the fact that it contains at least one additive selected from among antibiotics, sweeteners, moisteners or refreshants, preservatives, dyes, flavors, aromatizing or sapidity substances and agents, peptizing agents, plasticizers, antibacterial or bactericidal agents, vitamins, anti-caries agents, anti-tartar agents, anti-plaque agents, anti-staining agents, cicatrizants, vasomotors, anti-bleeding agents, and gum-active agents.

8. The composition of claim 1, characterized by the fact that it further contains enzymes, and/or oxygen liberators, and/or bleaching agents.

9. The composition of claim 1, characterized by the fact that it further contains preservatives intended to preserve good bacteriological purity of the compositions.

10. A process for cleaning teeth characterized by the fact that at least one composition as defined in claim 1, is applied to the teeth with the use of a brush.

* * * * *